United States Patent [19]

Levine

[11] 4,072,151

[45] Feb. 7, 1978

[54] SANITARY NAPKIN

[76] Inventor: Faye E. Levine, 257 Main St., Eagle Pass, Tex. 78852

[21] Appl. No.: 775,964

[22] Filed: Mar. 9, 1977

Related U.S. Application Data

[63] Continuation-in-part of Ser. No. 556,195, March 31, 1975, abandoned.

[51] Int. Cl.² ............................................. A61F 13/16
[52] U.S. Cl. .............................. 128/290 R; 128/290 P
[58] Field of Search ................... 128/284, 287, 290 R, 128/296, 290 P, 168

[56] References Cited

U.S. PATENT DOCUMENTS

| | | | |
|---|---|---|---|
| 3,411,504 | 11/1968 | Glassman | 128/290 R |
| 3,563,242 | 2/1971 | Hedstrom | 128/287 |
| 3,651,809 | 3/1972 | Champaigne | 128/290 R |
| 3,724,466 | 4/1973 | Hendricks | 128/290 R |
| 3,736,931 | 6/1973 | Glassman | 128/290 R |
| 3,769,979 | 11/1973 | Freney | 128/290 R |
| 3,830,237 | 8/1974 | Bernardin | 128/270 |
| 3,906,952 | 9/1975 | Zamist | 128/290 R |
| 3,927,673 | 12/1975 | Taylor | 128/287 |

FOREIGN PATENT DOCUMENTS

| | | | |
|---|---|---|---|
| 1,126,776 | 7/1956 | France | 128/284 |

Primary Examiner—Aldrich F. Medbery
Attorney, Agent, or Firm—Ted D. Lee

[57] ABSTRACT

A catamenial napkin conforming to the female body shape may be secured to the wearer without a supporting belt. The napkin has a backing formed from an impermeable plastic-like material. The longitudinal ends of the napkin have non-irritating adhesive strips that may attach the napkin to the body. The sanitary napkin has at least two layers of absorptive material separated by a perforated layer of otherwise impermeable material. The outer layer of absorptive material is covered by a non-irritating gauze. The napkin is completely filled with absorptive material to each longitudinal end, and is held together by non-irritating adhesive strips along each longitudinal edge.

3 Claims, 6 Drawing Figures

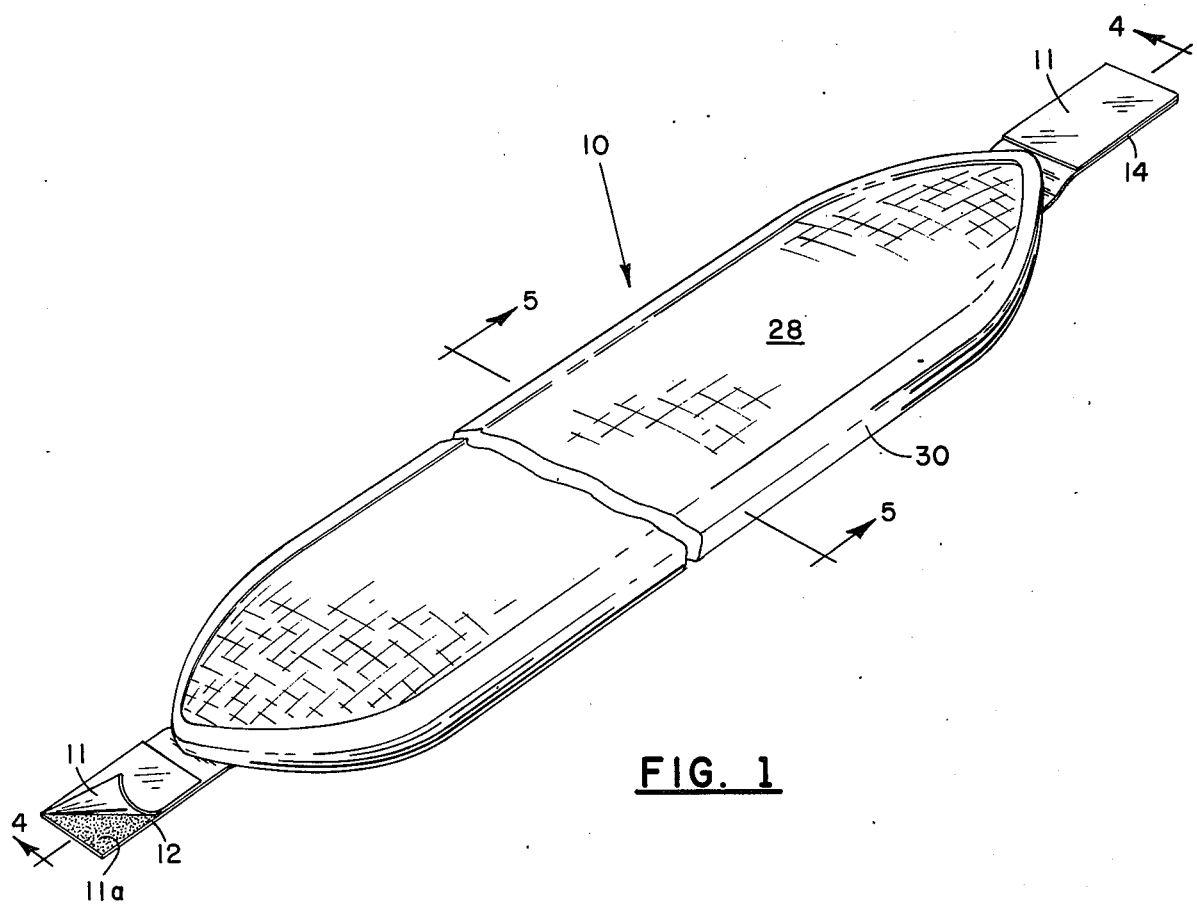
FIG. 1
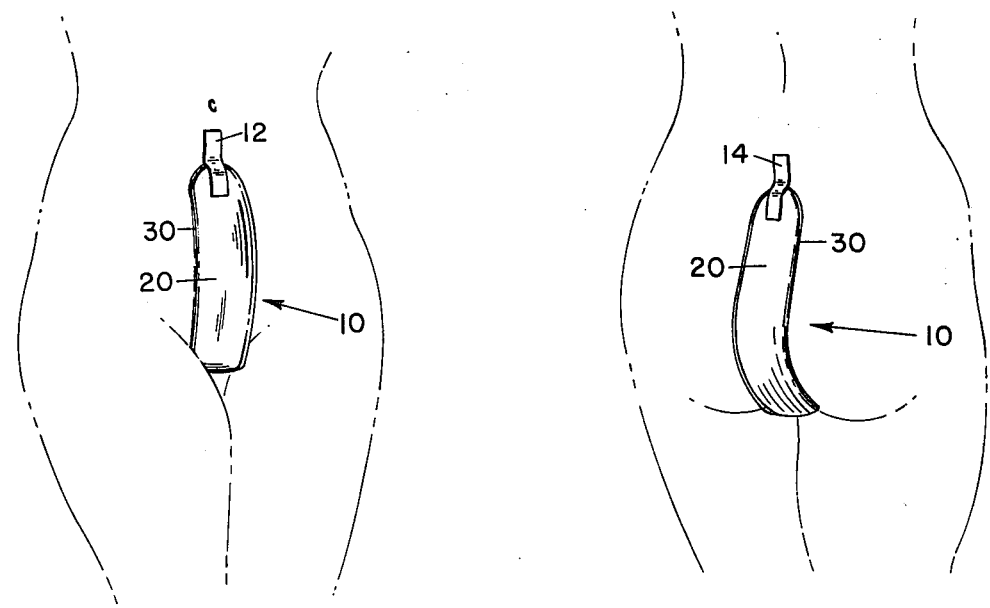
FIG. 2
FIG. 3

SANITARY NAPKIN

BACKGROUND OF THE INVENTION

This application is a continuation-in-part of U.S. patent application Ser. No. 556,195 filed on Mar. 31, 1975 by the same inventor, which application is hereby expressly abandoned upon the filing of this application.

This invention relates generally to sanitary napkins and, in particular, to a sanitary napkin that may be adhesively secured to the wearer thereby dispensing with the need for supporting belts. The present napkin is more absorbent and longer lasting, plus adjustable to the required snugness of the wearer.

BRIEF DESCRIPTION OF THE PRIOR ART

In women, the menstrual cycle is commonly repeated every 4 weeks from the time of puberty to menopause. Two types of commercially available catamenial devices are currently in use for the purpose of absorbing or stopping the menstruous flow; namely the tampon and the sanitary napkin. While tampons seem to offer marked advantages over sanitary napkins, their use is not always possible. For example, the tampon is not acceptable after childbirth, nor can it be used in post-surgical periods or when pathological conditions exist. The tampon is also inadequate when menstrual flow is heavy because of its limited capacity to abosrb secretions.

The tampon is a piece of cotton or other absorbent material, insertable in the vaginal opening. The sanitary napkin is not inserted, but is commonly held in place by means of a supporting belt or attached to the undergarment by means of an adhesive tape. These methods of securing the sanitary napkin exhibit a number of serious drawbacks. The belt may twist and turn causing irritation and chafing. The belt itself may be visibly outlined under normal clothing thereby revealing that the woman is menstruating. The sanitary napkin may also cause irritation and chafing of the skin, especially if it is not securely fastened. Attaching the napkin to the undergarment presents additional drawbacks. The napkin will tend to move with the undergarment rather than the body, resulting in a less secure fit and increased irritation and chafing. Removing the sanitary napkin from the undergarment can also be a messy procedure, sometimes resulting in the tearing or staining of the undergarment.

In the construction of sanitary napkins, an important objective is to control the absorption and flow of exudate in a manner which obtains maximum utilization of the available absorbent capacity of the napkin. Ideally, a sanitary napkin is exected to (1) immediately accept all exudate discharged on its top surface, (2) rapidly transport the exudate away from the point of discharge, (3) contain the transported exudate within the marginal confines of the napkin until substantially all of the absorbent capacity is used, and (4) maintain the body contacting surface of the napkin as dry as possible.

Sanitary napkins are available in various sizes, but the modern trend is toward smaller and inconspicuous napkins. While the smaller napkin may be more desirable for modern dress styles, it contains less absorbent material and is prone to leak and stain the undergarments. Thus a small sanitary napkin cannot perform the expected functions listed above without frequent and regular changing.

While the sanitary napkin may be preferable in many respects to the tampon, the practical and aesthetic disadvantages of existing designs are displeasing, so that many women make use of tampons even though their requirements would be better served by sanitary napkins. If unable to use tampons, many women are forced to use sanitary napkins that simply do not do the job.

SUMMARY OF THE INVENTION

The improved sanitary napkin of this invention is made up of an elongate multilayered pad element, in which the element consists of two absorption layers of cotton-like material separated by a sheet of perforated plastic. The pad element is approximately four inches wide and fifteen to eighteen inches long filled throughout with absorptive material. A full-length fluid impermeable sheet of plastic envelopes the lower half of the napkin extending around and over the marginal sides of the napkin. The top absorption layer of the napkin is covered with a non-irritating gauze-like material. The sides of the napkin are enclosed by a paper-like, non-irritating adhesive to prevent chafing and irritation of the skin. The pad element is also equipped with two strips of peel-off tape tabs which are skin adherring, but non-irritating. The tape tabs may be applied vertically or horizontally to the skin as desired along the ends of the napkin. If a person desires to use a supporting belt, the tape tabs may be applied to the supporting belt, but the napkin may move out of position due to normal body movment.

Exudate striking the gauze-like layer is immediately transported to the top absorption layer. As the top absorption layer becomes saturated, the perforated sheet evenly distributes the exudate to the lower absorption layer. Even dispersal prevents bleed-through and staining of the undergarment. The long length of the sanitary napkin of this invention increases its absorptive capacity thus reducing the number of required changings.

It is main object of this invention to provide an improved sanitary napkin.

It is another object of this invention to provide an improved sanitary napkin that does not require a supporting belt.

It is yet another object of this invention to provide non-irritating, skin adhesive tape strips for securing a sanitary napkin to the body of the wearer.

It is still another object of this invention to provide a sanitary napkin employing a perforated sheet between absorbent layers for effective and even dispersal of exudate to both absorbent layers.

It is still another object of this invention to provide a sanitary napkin which functions effectively, yet it may be worn comfortably without chafing or irratating the skin.

BRIEF DESCRIPTION OF THE DRAWINGS

FIG. 1 is a perspective view of a sanitary napkin showing a preferred embodiment of this invention.

FIG. 2 is a frontal environmental view illustrating position and connection of the sanitary napkin.

FIG. 3 is a rear environmental view illustrating position and connection of the sanitary napkin.

DETAILED DESCRIPTION OF THE PREFERRED EMBODIMENT

Figure 4:
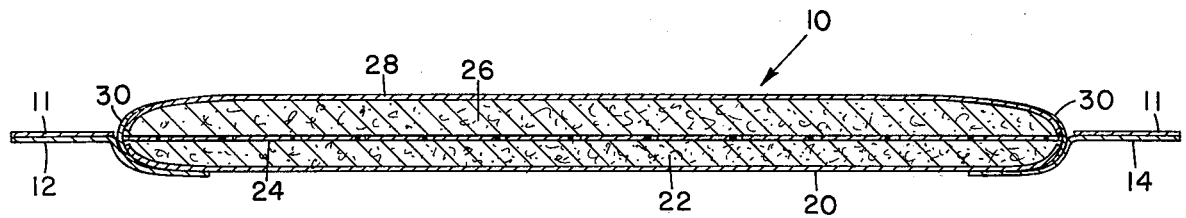
FIG. 4 is a sectional view taken along section lines 4—4 of FIG. 1.

Catamenial napkins are universally used by women with varying success. Some women find the modern trend toward smaller, inconspicuous napkins convenient, and use the smaller napkins with a great deal of success. However, some women, especially those with heavy menstrual flow, have found that the smaller inconspicuous napkins, although more desirable, simply do not do the job.

Referring now to the drawings, there is shown a sanitary napkin in accordance with the invention. The napkin, as shown in FIG. 1, is an elongated pad element generally designated by numeral 10. When properly attached to the body of the wearer, tab 12 is taped in front just below the navel as shown in FIG. 2, and tab 4 is taped to the small of the back above the cleavage of the buttocks as shown in FIG. 3.

Figure 6:
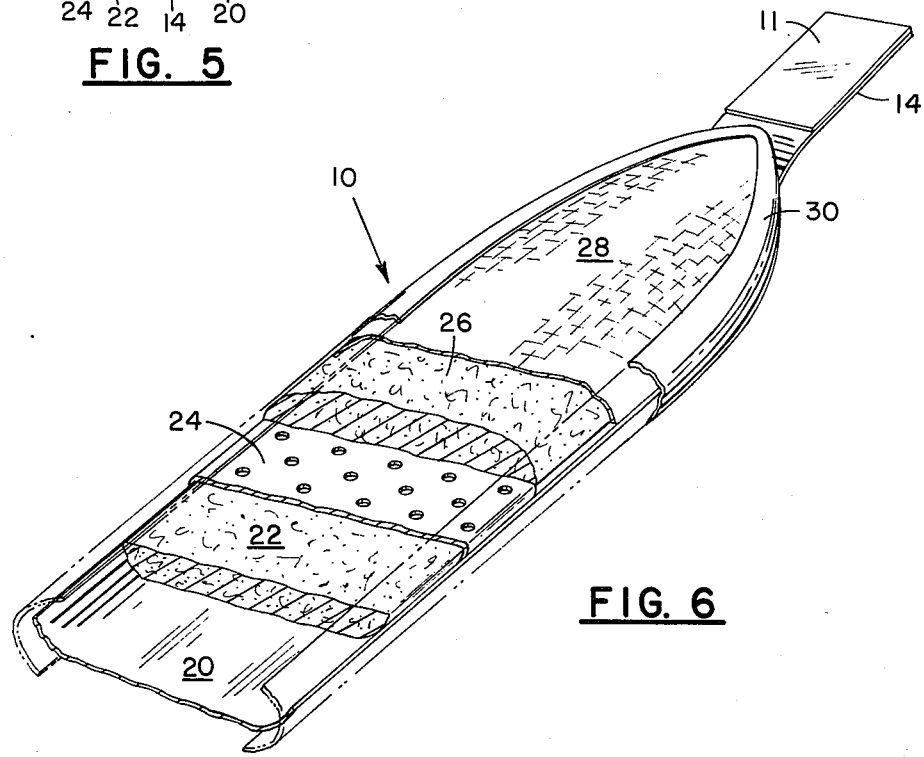
FIG. 6 is a perspective view partially broken away to show internal construction of the sanitary napkin.

Tha napkin 10, as shown in FIG. 6 is backed by an impermeable sheet of plastic 20 extending around and over the marginal sides of the napkin 10. Bottom absorption layer 22 is covered by a plastic perforated sheet 24. The function of perforated sheet 24 is to evenly distribute the body fluid exudate from top absorption layer 26 to bottom absorption layer 22, thus avoiding a localized area of saturation at the point of discharge. Without perforated sheet 24, discharged exudate would quickly penetrate the layers of absorptive material and from a localized area of saturation at the point of discharge. As noted many times in the prior art, localized saturation is considered undesirable. As top absorption layer 26 becomes saturated, the exudate will penetrate to perforated sheet 24 and seep through the holes in perforated sheet 24 to bottom absorption layer 22. While the configuration of the holes in perforated sheet 24 can be varied, the holes should be spaced far enough apart to avoid the localizing effect discussed above.

Gauze layer 28 covers top absorption layer 26 and extends over the marginal sides of the napkin 10. In the preferred embodiment, gauze layer 28 is a fluid-permeable material retaining little, if any, of the exudate discharged, which maintains the contact area between the gauze layer 28 and the wearer as dry as possible.

To avoid chafing and irritation of the skin, a paper-like tape 30, as shown in FIG. 6, encloses the napkin 10 around its marginal sides. Tape 30, which is non-irritating, prevents plastic layer 20 which extends over and around the marginal sides of the napkin 10 from irritating the inner thighs of the wearer.

Figure 5:
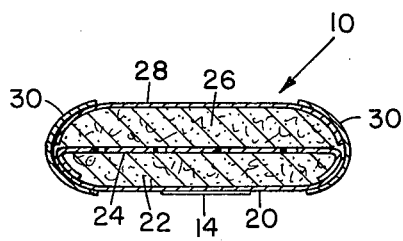
FIG. 5 is a sectional view taken along section lines 5—5 of FIG. 1.

FIGS. 4 and 5 are sectional view of the invention showing absorption layers 22 and 26 and perforated sheet 24 extending the full length and width of the napkin 10. Also shown in FIG. 5 is tape 30 enclosing the marginal sides of the napkin 10 at the junction of gauze layer 28 and plastic layer 20.

Referring again to FIG. 1, tape tab 12 is shown at one end of the napkin 10. The adhesive side 11a of tape tab 12 is covered with a protective sheet 11 which is peeled off only before securing tape tab 12 to the skin of the wearer. The adhesive side 11a of tape tabs 12 and 14 is of the type used in high quality, plastic surgical bandages. Tape tabs 12 and 14 are non-irritating to the skin and remain securely attached to the skin of the wearer until deliberately removed.

While there has been shown and described a preferred embodiment of a sanitary napkin in accordance with the invention, it will be appreciated that many changes and modifications may be made therein without, however, departing from the essential spirit of the invention. The absorption layers 22 and 26 may be made from any suitable absorbent material, such as cotton.

I claim:

1. A sanitary napkin for controlling the dischage of body fluid exudate comprising:
    pad element having a top absorption means and a bottom absorption means;
    backing means attached to the bottom of said pad element, said backing means being an impervious material, said bottom absorption means being a layer of absorptive material in direct contact with said backing means, said top absorption means being a layer of absorptive material in fluid communication with said bottom absorption means;
    means for dispersing and preventing localized body fluid exudate saturation of said top absorption layer means and even exudate distribution to said bottom absorption layer means comprising sheet means of an impervious material between said bottom absorption means and said top absorption means, said sheet means separating said entire top absorption means from said entire bottom absorption means, said sheet means being perforated to allow for rapid and even transfer of fluids from said entire top absorption means to said entire bottom absorption means;
    adherring means attached to the longitudinal ends of said pad element, said adherring means being a non-irritating adhesive adapted for attachment to the body of the wearer; and
    facing means attached to the top of said pad element, said facing means being a fluid pervious gauze-like material, said bottom absorption means and said top absorption means extending essentially the full width and length of said sanitary napkin.

2. A sanitary napkin or the like as given in claim 1 wherein marginal sides of said pad element are enclosed by a non-chafing, non-irritating tape.

3. A sanitary napkin or the like as given in claim 2 wherein said adherring means is detachable for adjusting snugness of said pad element to the body of the wearer.

* * * * *